(12) United States Patent
Evans et al.

(10) Patent No.: US 11,786,416 B2
(45) Date of Patent: *Oct. 17, 2023

(54) QUICK RELEASE, BACK CARRY, FIRST AID KIT

(71) Applicant: Edge-Works Manufacturing Company, Burgaw, NC (US)

(72) Inventors: Scott V. Evans, Jacksonville, NC (US); David Pomeroy, Tamarac, FL (US); Jesse Lockhart, Hampstead, NC (US)

(73) Assignee: Edge-Works Manufacturing Company, Burgaw, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/650,790

(22) Filed: Feb. 11, 2022

(65) Prior Publication Data

US 2022/0160556 A1    May 26, 2022

Related U.S. Application Data

(63) Continuation of application No. 16/868,611, filed on May 7, 2020, now Pat. No. 11,259,971, which is a continuation of application No. 16/242,725, filed on Jan. 8, 2019, now Pat. No. 10,675,196.

(60) Provisional application No. 62/614,845, filed on Jan. 8, 2018.

(51) Int. Cl.
| | |
|---|---|
| *A61F 17/00* | (2006.01) |
| *A45F 3/02* | (2006.01) |
| *A45F 5/02* | (2006.01) |
| *A45F 3/14* | (2006.01) |
| *A45F 5/00* | (2006.01) |

(52) U.S. Cl.
CPC ............... *A61F 17/00* (2013.01); *A45F 3/02* (2013.01); *A45F 3/14* (2013.01); *A45F 5/021* (2013.01); *A45F 2003/142* (2013.01); *A45F 2005/008* (2013.01)

(58) Field of Classification Search
CPC ..... A45C 2011/007; A45C 13/02; A45C 1/04; A45C 7/0095; A45C 13/30; A45C 7/0054; A45C 11/26; A61F 17/00; A45F 5/021; A45F 2005/008; A45F 2005/006
USPC ................. 224/223, 663, 677, 220
See application file for complete search history.

(56) References Cited

U.S. PATENT DOCUMENTS

| | | | | |
|---|---|---|---|---|
| 1,260,539 A | * | 3/1918 | Hertz ................... | G04B 37/127 |
| | | | | D10/128 |
| 1,438,145 A | * | 12/1922 | Swartz .................... | A45C 1/04 |
| | | | | 224/220 |
| 2,679,877 A | * | 6/1954 | Leggett .................... | B42F 7/04 |
| | | | | 383/39 |

(Continued)

*Primary Examiner* — Adam J Waggenspack
(74) *Attorney, Agent, or Firm* — Intellectual Property Consulting, LLC; Stephen M. Kepper

(57) ABSTRACT

The present invention relates in general to portable first aid kits and, in particular, to a low profile first aid kit that is adaptable for a quick release from a carrier and can be easily stored and carried by a person. The design of the disclosed release system allows for the first aid kit to be released with one hand from a carrier with mounting capabilities. Additionally, the medical kit includes a dual purpose carrier strap that can either be wound around the first aid kit and operable to torque the kit for storage purposes when in the closed position, or used to carry the kit in the open position until it can be secured and subsequently stored.

11 Claims, 10 Drawing Sheets

(56) References Cited

U.S. PATENT DOCUMENTS

| | | | | |
|---|---|---|---|---|
| 3,389,784 | A * | 6/1968 | Hendricks | A61F 17/00 206/573 |
| 4,738,547 | A * | 4/1988 | Brown | A45C 7/0095 383/119 |
| 5,269,410 | A * | 12/1993 | Abregano | A63B 57/203 206/315.5 |
| 6,244,486 | B1 * | 6/2001 | Holland | A45F 5/02 224/223 |
| 8,267,289 | B2 * | 9/2012 | Irvin | A45F 5/00 224/267 |
| 9,504,615 | B2 * | 11/2016 | Beikoff | A61F 5/3738 |
| 10,306,973 | B2 * | 6/2019 | Evans | A45F 5/02 |
| 2002/0038811 | A1 * | 4/2002 | Vigny | A45F 3/04 224/651 |
| 2008/0121554 | A1 * | 5/2008 | Townsend | A45C 5/02 206/570 |
| 2011/0017624 | A1 * | 1/2011 | Robertson | A45C 13/02 206/438 |
| 2016/0209163 | A1 * | 7/2016 | VanHeusen | A45F 5/00 |
| 2019/0099187 | A1 * | 4/2019 | Theodorou | A45C 7/0077 |

* cited by examiner

QUICK RELEASE, BACK CARRY, FIRST AID KIT

RELATED APPLICATIONS

This application is a continuation of U.S. application Ser. No. 16/868,611, filed May 7, 2020, which is a continuation of U.S. application Ser. No. 16/242,725, filed Jan. 8, 2019, which claims priority to U.S. Provisional Application No. 62/614,845 filed Jan. 8, 2018. The entire contents of the above applications are hereby incorporated by reference as though fully set forth herein.

FIELD

The present invention relates in general to portable first aid kits and, in particular to a low profile first aid kit that is adaptable for a quick release and can be easily stored and carried by a person.

BACKGROUND

First aid kits generally contain items that are used as a means to quickly and effectively respond to accidents or injuries when away from traditional medical emergency facilities. Such kits are intended to be used either by the injured party or to aid someone else. These kits must be lightweight, portable, accessible, and must contain the necessary equipment to treat accidents or injuries that may occur based on the situation and environment. This is very critical for military or law enforcement environments, where the threat of accident or injury is high and access to medical treatment is very limited.

For example, military personnel are provided with individual first aid kits (IFAK) during times of military deployment. Such kits are typically housed in cloth bags or pouches and are worn on the outside of a uniform. Such IFAKs are intended to increase an individual soldier's capability to provide self-aid on the battlefield.

Current first aid kits are either carried on a belt strap, as a back pack with straps, or leg strap to allow for freedom of movement and access to the contents of the pouch. This often makes it difficult for the soldier or law enforcement officer to get to the contents of the pouch when only one hand is available.

Another shortfall of the current aid kits, is that during times of high stress and rapid combat deployment, it may be inadvertently left behind, as it is one more piece of equipment that a solider or enforcement officer must remember to attach to a uniform rather than having an alternative way to carry the kit until it can be reattached.

Typical protective vests are manufactured from "soft-armor" materials such as Kevlar® or other "bullet proof" materials and offer a level of protection to the wearer sufficient to offer protection in many situations. For the additional security required in today's military and law enforcement applications; however, soft armor is often insufficient against military munitions and shrapnel. Accordingly, many protective vests or body armor vests contain a series of external pockets on the front, back and sides of the vest for adding additional body armor such as metal or ceramic plates, also known as ballistic plates or hard armor. The plates are usually placed to cover particularly vulnerable parts of the body such as the heart, chest, and back regions, thereby providing protection to the vital organs.

The use of kits containing a select number of products appropriate for use in first aid conditions that attach to these plates or the exterior of body armor vests of military personnel, law enforcement and first responders are known in the prior art. However, these kits are often bulky and are made for attachment to the front of the user, taking up valuable space for tactical gear. Further, removal of these kits requires the use of both hands of the user.

As such, there is a need for a portable first-aid kit that can be mounted in a convenient location on the user and includes an easily accessible quick-release mechanism that allows the user access to medical supplies with only one hand. When finished, the current device also allows the user a means to quickly store the kit or a convenient way to carry the kit until the user has sufficient time to re-mount the kit to their person.

BRIEF SUMMARY OF THE INVENTION

The present invention is a compact first aid kit that provides an individual with the necessary lifesaving equipment to effectively treat injuries commonly associated with combat. The innovative design of the pouch pillow release system allows for the kit to be released with one hand and mounted either vertically or horizontally to any carrier, plate or vest surface, especially the back. Placement on the back allows the user to take advantage of unused space and prioritize individual equipment layout. Additionally, a shoulder strap allows the first aid kit to be easily carried until it is remounted to the carrier or vest surface.

DETAILED DESCRIPTION

Figure 1:
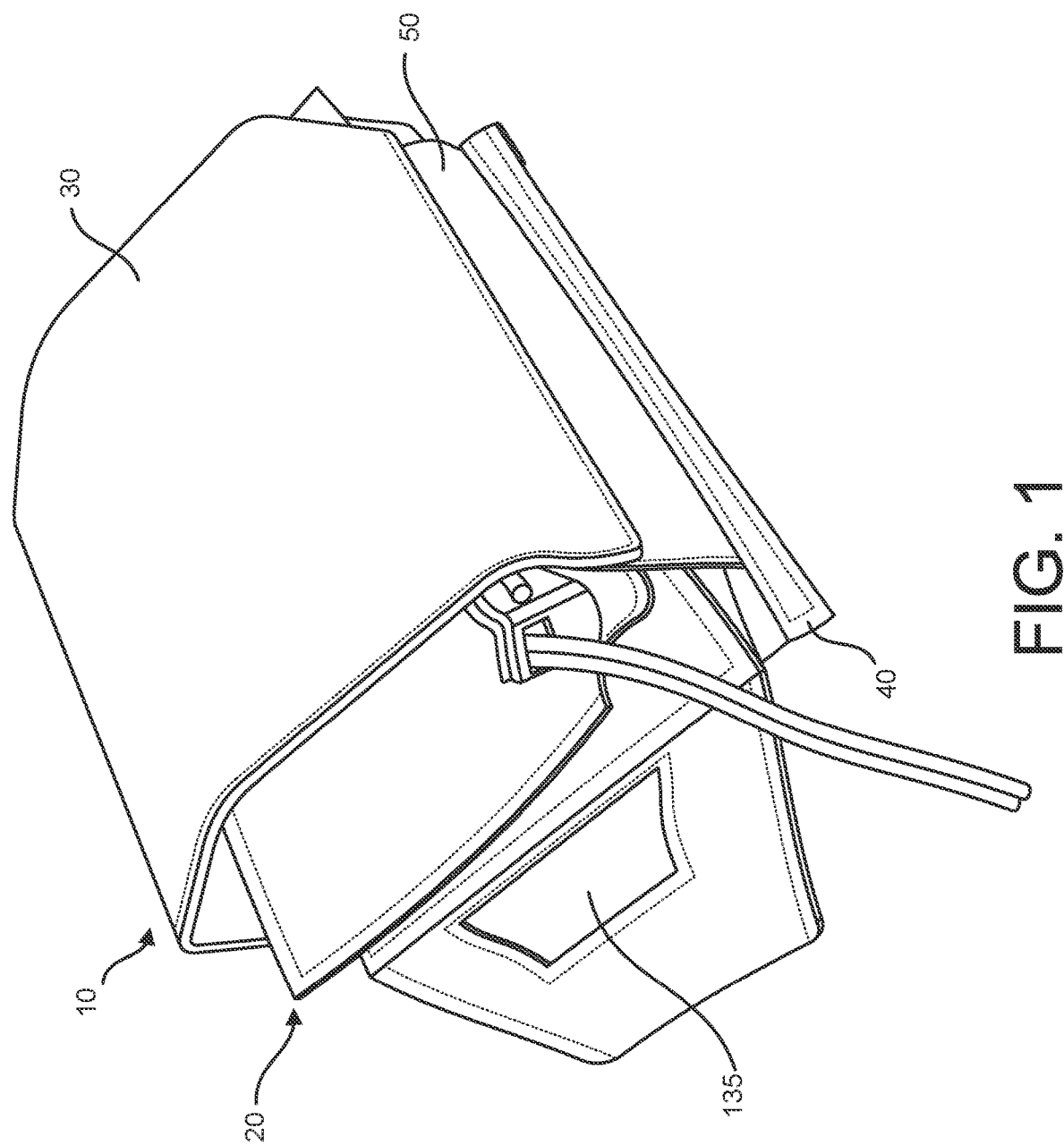
FIG. 1 is a perspective front view of the carrier showing the first aid kit stored within the carrier.
Figure 2:
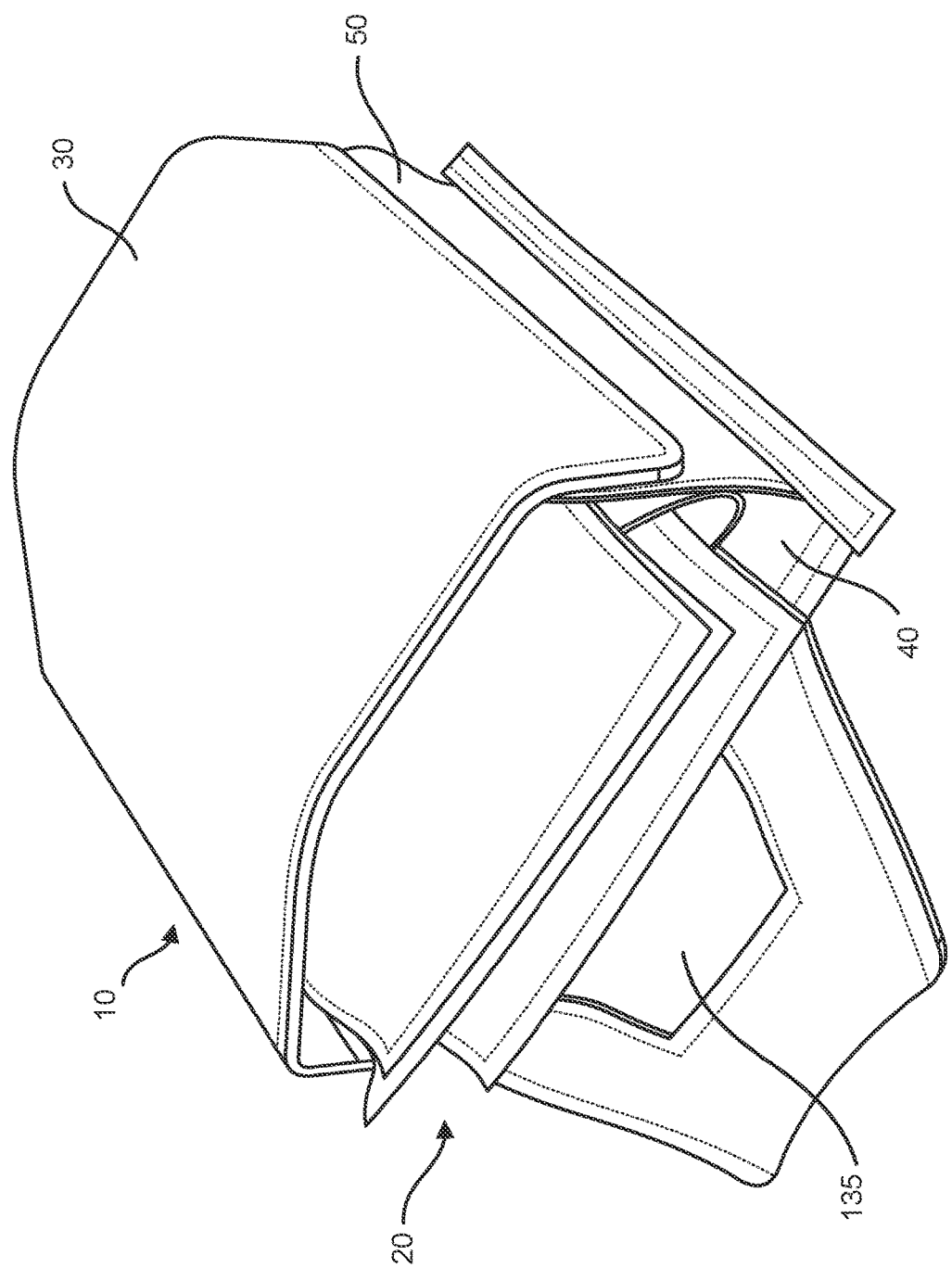
FIG. 2 is an alternative perspective front view of the carrier showing the first aid kit stored within the carrier and showing the other side of the carrier and kit not visible in FIG. 1.

As shown in FIGS. 1-4, the present invention comprises a hollow carrier 10 for storing a first aid kit 20 comprising a front portion 30 and a back portion 40 connected by at least one elastic, pliable connecting member 50 that forms a portion of opposing top and bottom walls, which define a hollow interior compartment 100. Turning to FIG. 5, the elastic, pliable member 50 may be made from fabric, including Nylon, or any other type of fabric or material with similar properties. In the preferred embodiment, the front portion 30 is substantially rigid and further comprises a front surface 60 intersecting two opposing sides 70 that extend longitudinally along a portion of the opposing top and bottom walls and connect to the elastic members 50 forming the remaining portion of the opposing top and bottom walls of the carrier; the rigidity of the front portion 30 allows the carrier to maintain its general shape. In order to provide rigidity, the front portion 30 may, for example, be made from thermoforming plastic or providing some type of plastic or other rigid material as an insert into a pliable covering. Although not required, the present invention anticipates the front surface 60 being substantially concave and protruding slightly outward in the direction opposite the hollow interior 100 of the carrier 10. The additional cross-sectional area provided by the protruding front surface 60 of the front portion 30 of the carrier 10 allows the first aid kit 20 to be easily reinserted into the carrier 10 while simultaneously displacing pressure evenly across the surface of the carrier 10. Alternatively, the carrier 10 may be completely collapsible where the front portion 30 is pliable, e.g, made from fabric or a malleable rubber or plastic.

Figure 3:
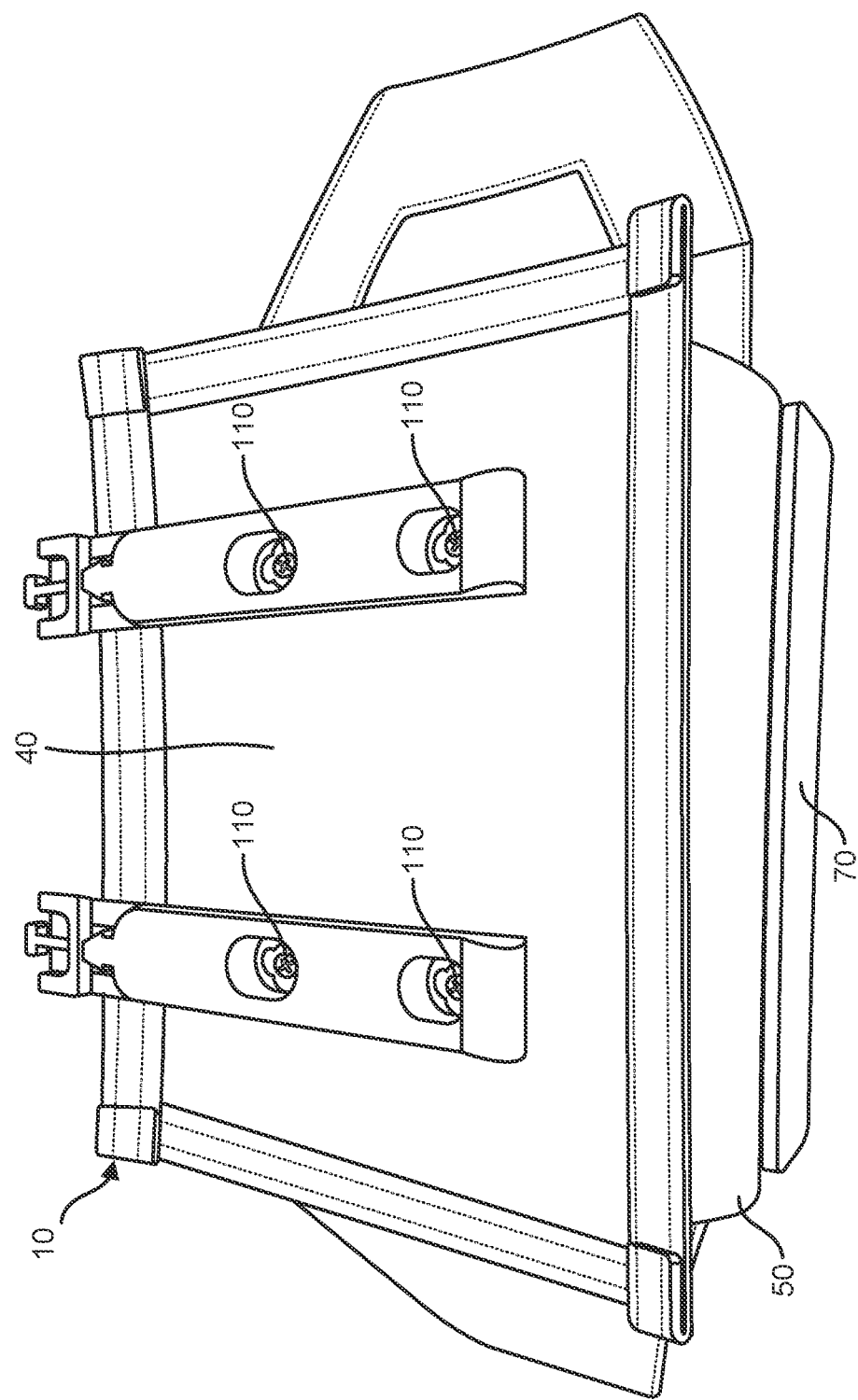
FIG. 3 is a perspective back view of the carrier showing the first aid kit stored within the carrier.
Figure 4:
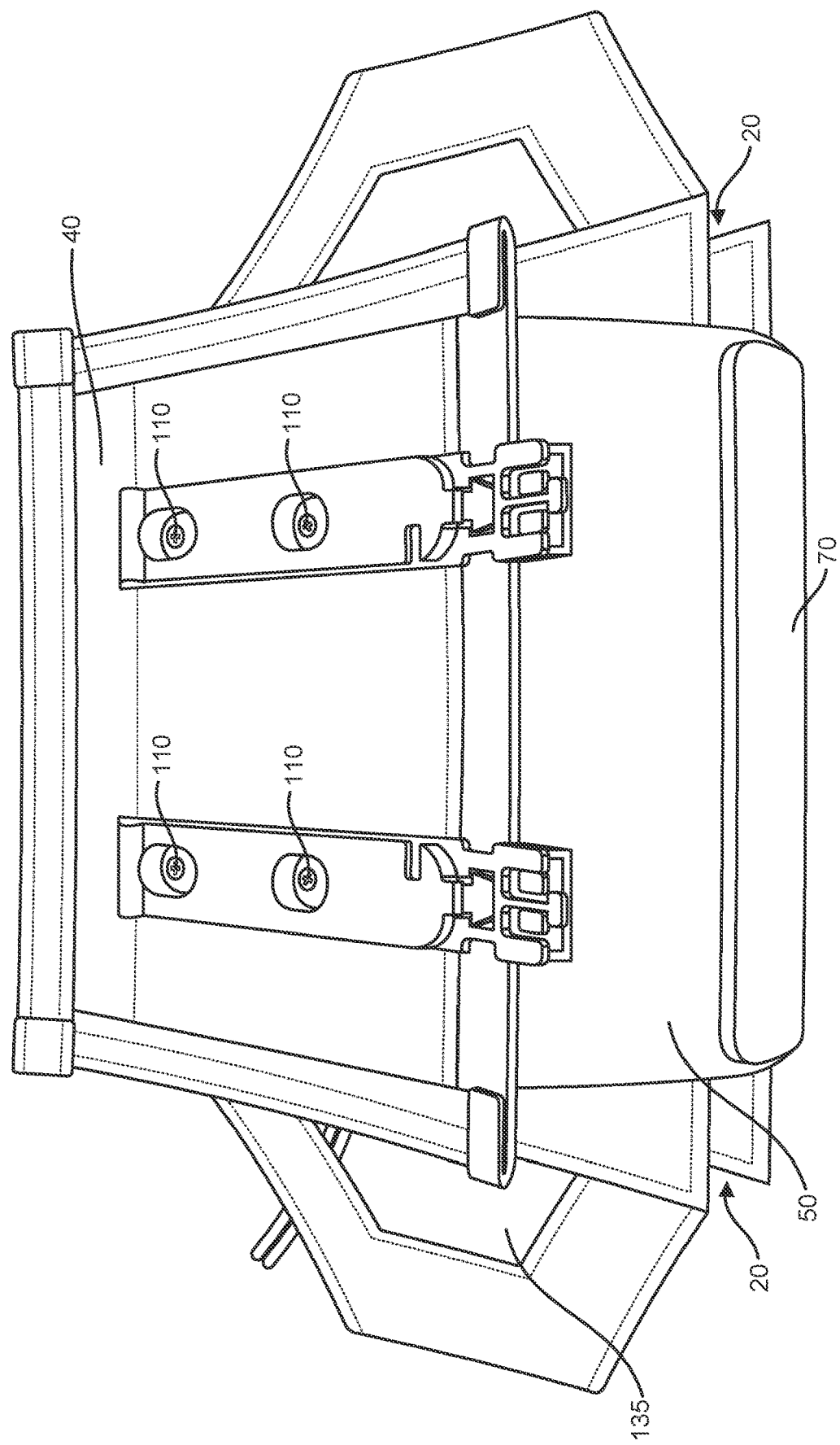
FIG. 4 is an alternative perspective back view of the carrier showing the first aid kit stored within the carrier and showing the other side of the carrier and kit not visible in FIG. 3.
Figure 5:
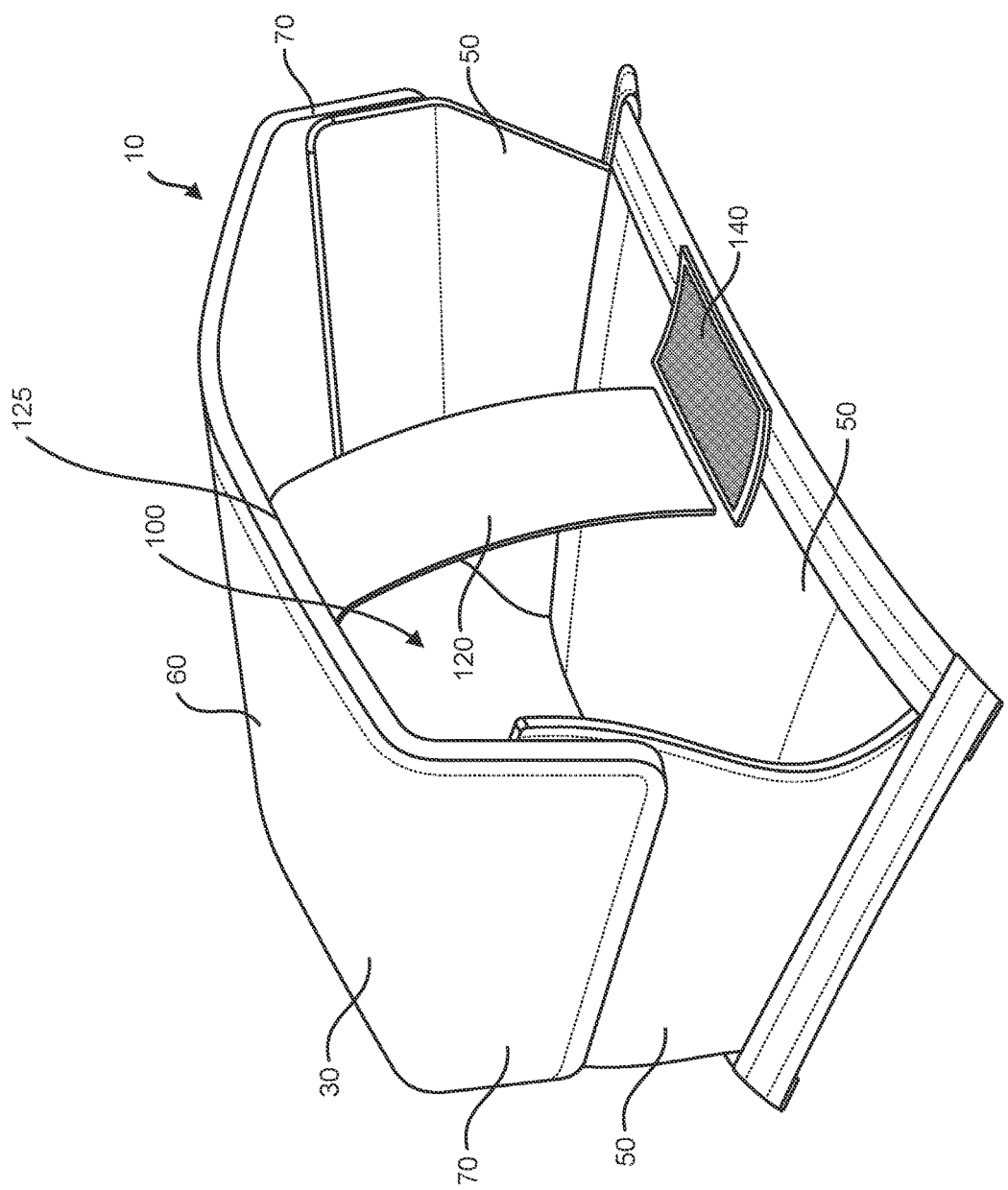
FIG. 5 is a perspective view of the carrier without the first aid kit.

Turning to FIGS. 3 and 4, the hollow carrier 10 comprises a plurality of molding mounting apertures 110 in or on the back portion 40 to enhance the scope and usefulness of the invention enabling it to be completely modular, useable with an entire family of mounting accessories. Such accessories include but are not limited to: paddles, clips, belt loops, MOLLE (modular, lightweight load-carrying equipment) attachment devices (e.g. the device shown in the figures and disclosed in U.S. patent application Ser. No. 15/481,393), leg mounts, vest carry, harness carry, etc. As shown in FIG. 5, the two open ends or sides of the carrier contain a closure strap 120 wherein one end of the strap is attached to the perimeter of the interior surface 125 of the front portion 30 and the other end is removably attached to perimeter of the interior surface 140 of the back portion 40. The attachment points could also be reversed wherein one end of the closure strap 120 is attached to the perimeter of the interior surface of the back portion 40 and the other end is removably attached to perimeter of the interior surface of the front portion 30. Although the preferred embodiment uses hook and loop fastening means, e.g. VELCRO®, to attach the closure strap 120 to the carrier, other types of fastening means are contemplated, including use of snap-buttons, quick-release clips, or any other quick-release fastener known in the art. The closure straps 120 of the carrier 10 are adapted to secure and retain the first aid kit 20 within the hollow carrier 10.

Figure 6:
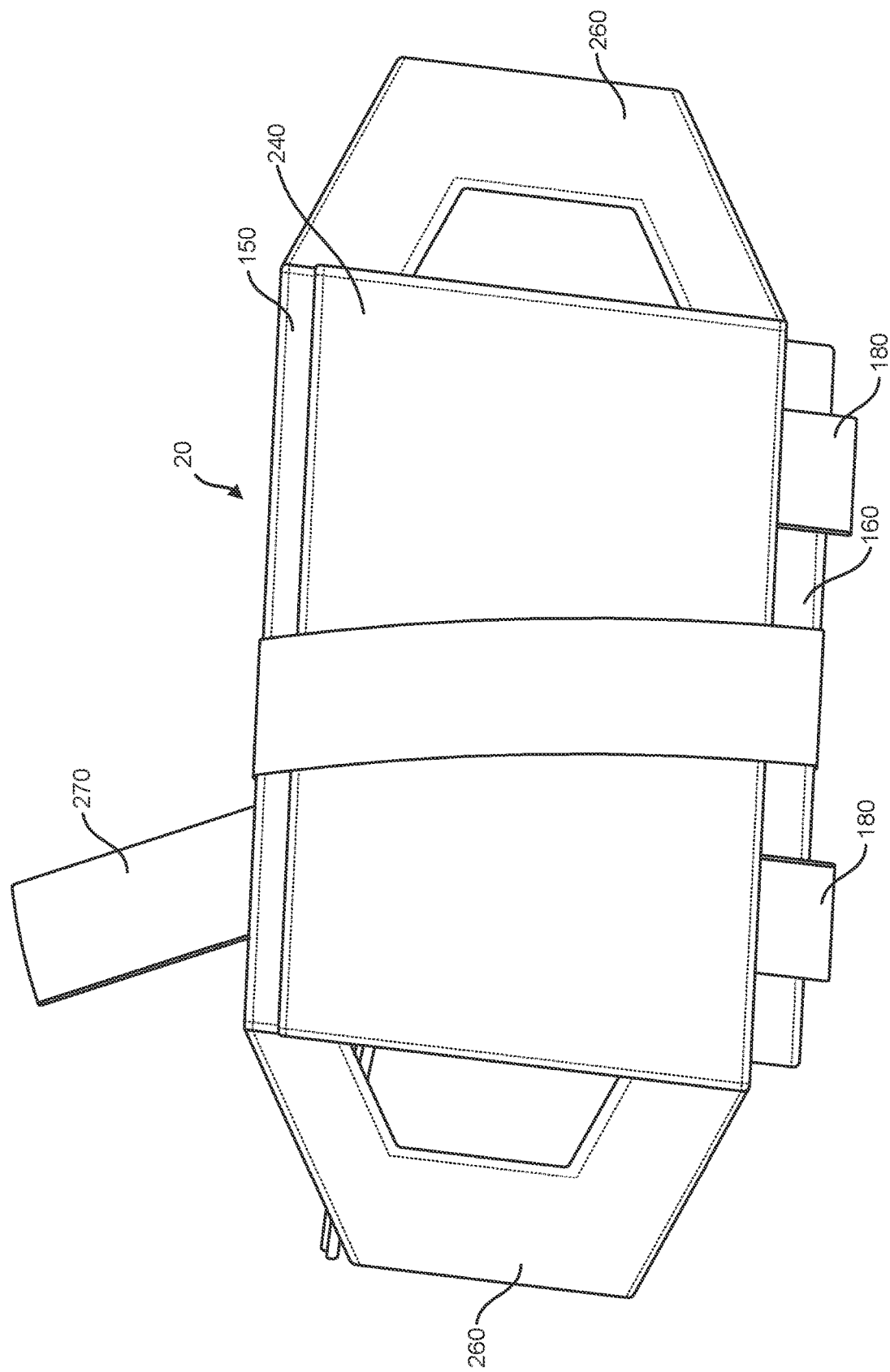
FIG. 6 is a perspective top view of the first aid kit shown in the closed and folded position with the carrier strap wrapped around it.
Figure 7:
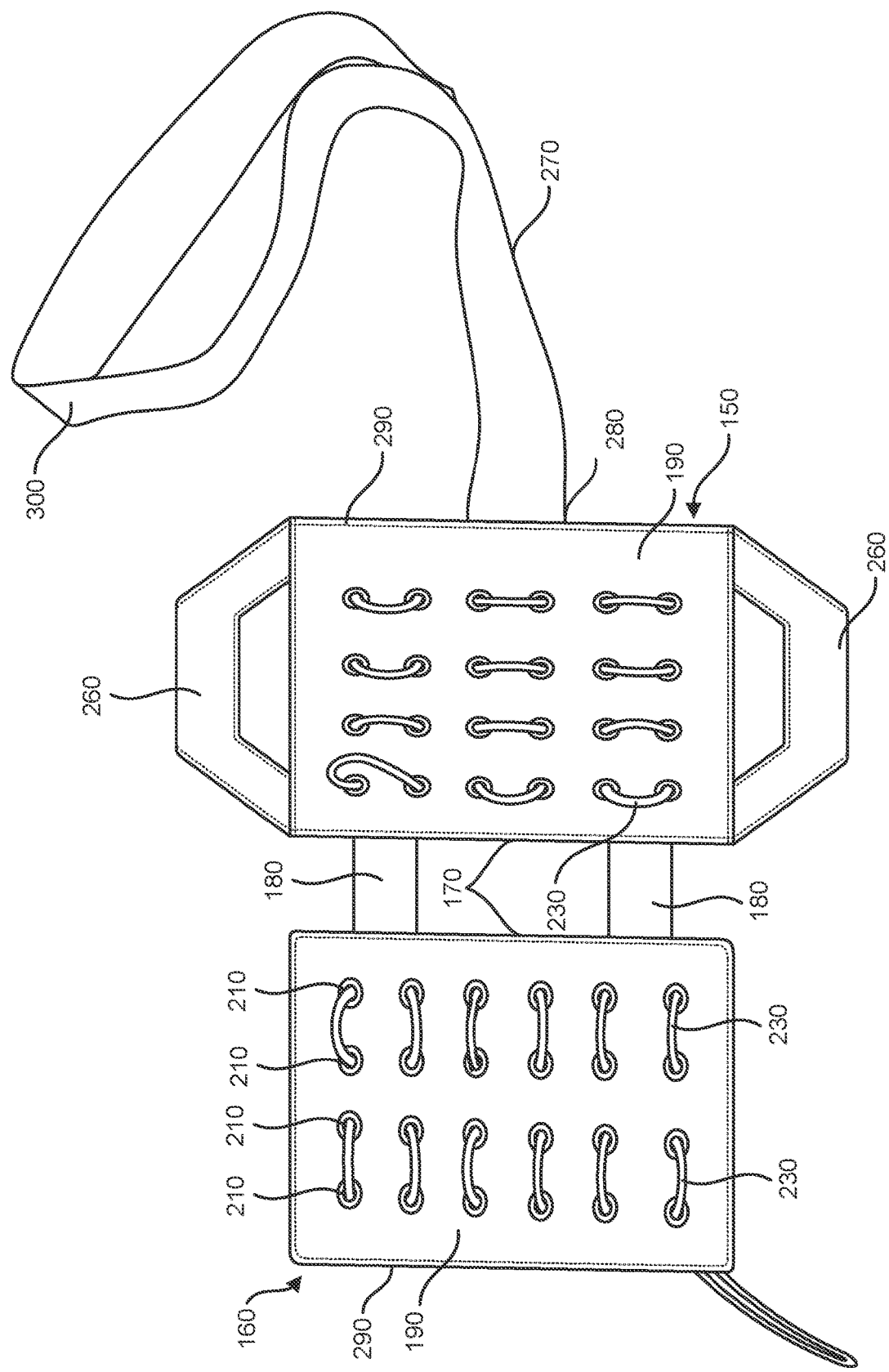
FIG. 7 is a top view of the first aid kit shown in the open, unfolded position.
Figure 8:
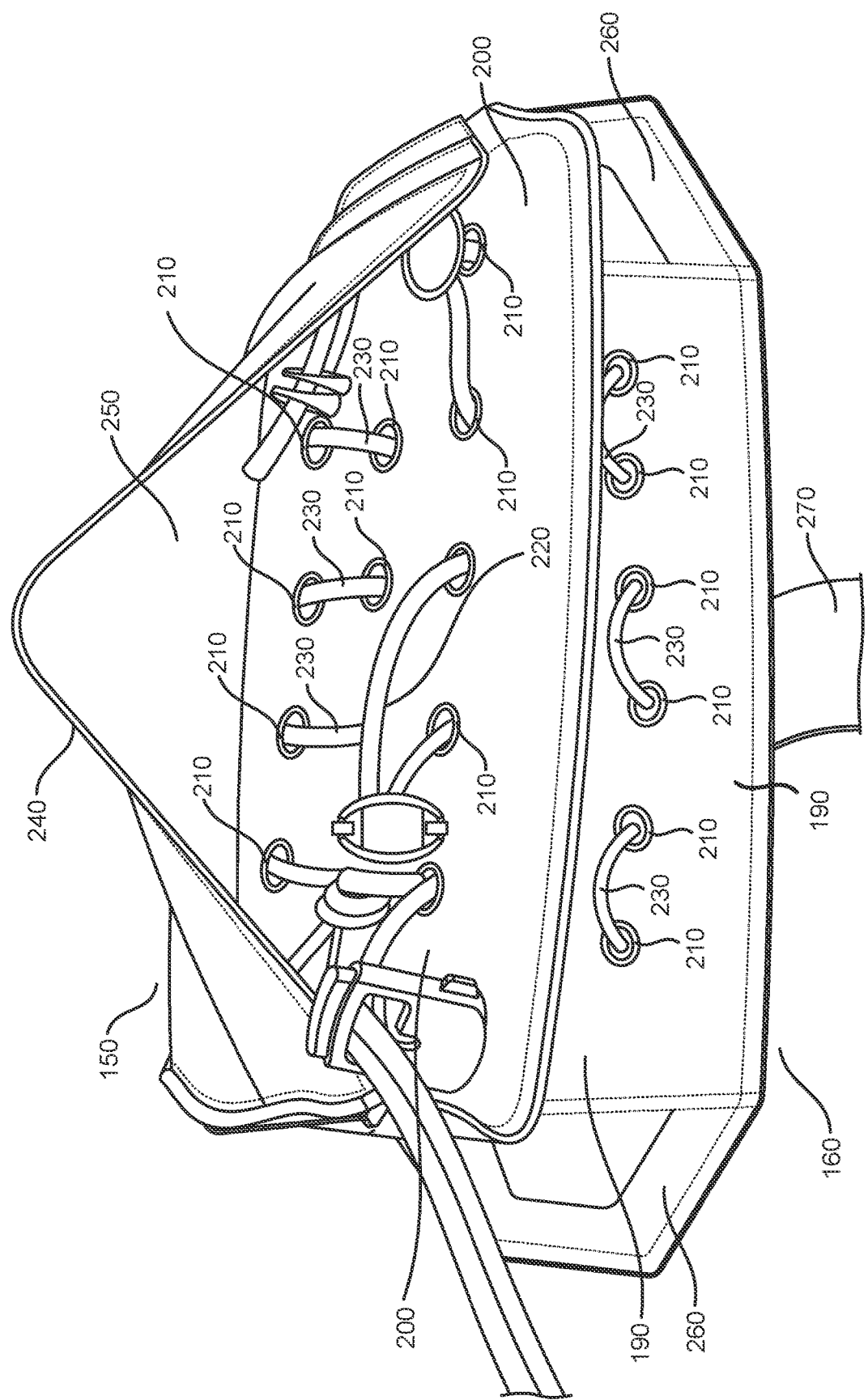
FIG. 8 is a perspective view of the first aid kit in the closed, folded position with the exterior surface of the bottom portion shown beneath the cover.
Figure 9:
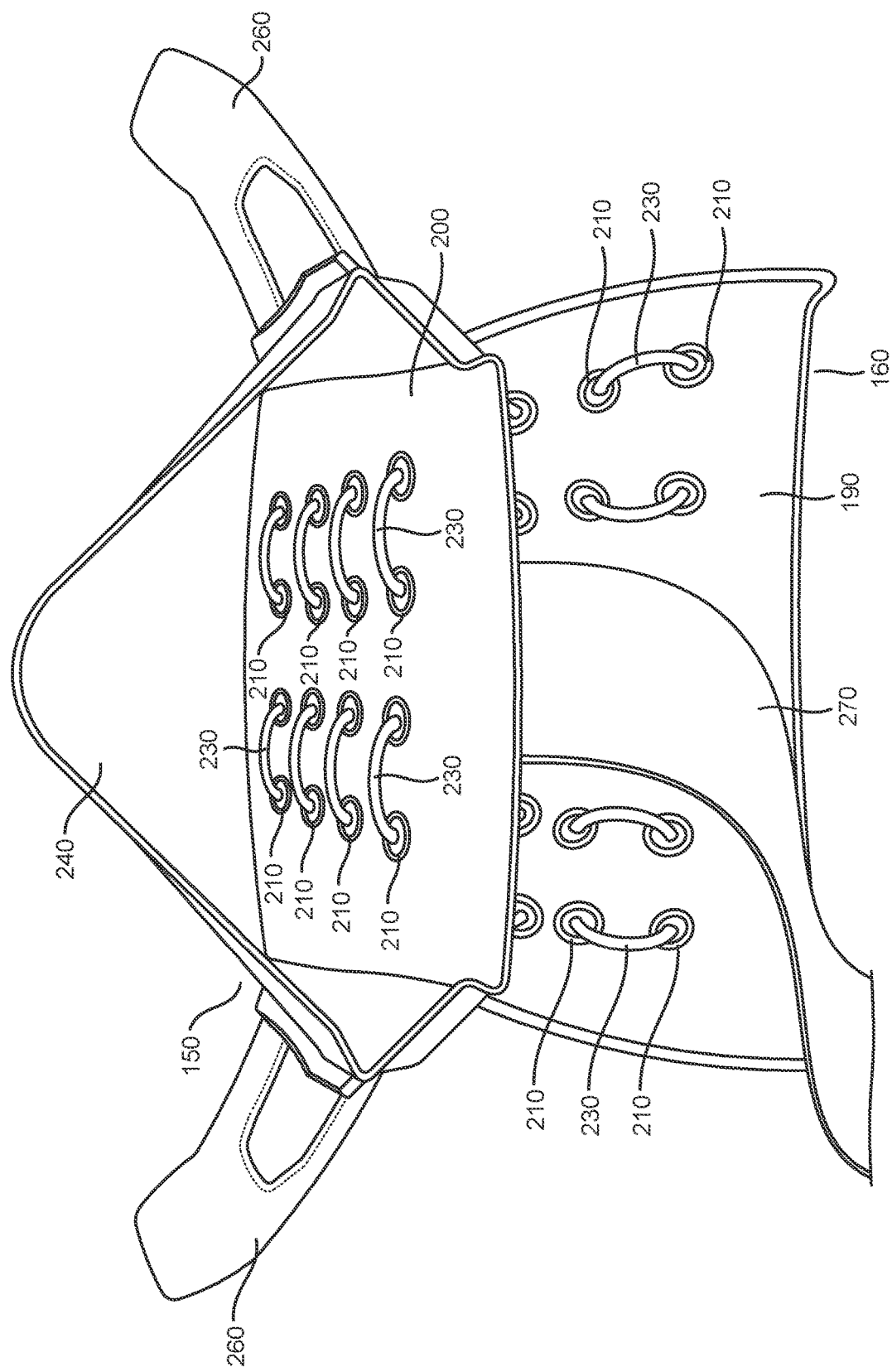
FIG. 9 is a perspective view of the first aid kit in the closed, folded position with the exterior surface of the top portion shown beneath the cover.

Turning to FIGS. 6-10, the first aid kit 20 stored within the carrier 10 comprises a top portion 150 and a bottom portion 160 that can be folded against each other along the proximal ends 170 of each portion 150, 160. As shown in the FIGS. 6-7, and 10, the first aid kit may utilize at least one pliable connection member 180 that attaches to each portion at their respective proximal ends 170 and functions as a hinge to the top 150 and bottom portions 160. The use of the flexible member 180 allows the first aid kit 20 to maintain its rectangular cross-sectional shape by keeping the top 150 and bottom portion 160 in substantial parallel alignment when medical items and products are stored on the interior surface 190 of each portion 150, 160. Turning to FIGS. 7-9, each portion 150, 160 further comprises a plurality of apertures 210 wherein a binding device 220, e.g. a bungee cord, is woven through the apertures 210 to create a series of loops 230 on the interior surface 190 and exterior surface 200 of both portions 150, 160. These loops 230 are used to store various emergency medical equipment. The elasticity of the binding device 220 allows the user to quickly retrieve and store these items for use in emergency situations. Although the preferred embodiment uses a binding device 220 woven through apertures 210, the present invention also anticipates using other fastening means known in the art for attaching equipment to either portion 150, 160, including hook and loop fasteners such as VELCRO®, snap-buttons, clips, or any other fastening device that may be used to secure portable equipment.

Optionally, a cover 240, as shown in FIGS. 8 and 9, may be attached along the perimeter of the exterior surface 200 of the top 150 or bottom portion 160 of the carrier wherein the cover 240 creates a pocket with an opening 250 to allow access to the stored contents within the loops 230 contained on the exterior surface 200 of either portion 150, 160. The cover 240 may be attached to the exterior surface 200 of either portion by any fastening means known in the art, including but not limited to, stitching fibers, weaving fibers, braiding fibers, riveting, gluing, or any type of fasteners known in the prior art such as hook and loop fasteners. As an additional option, the top 150 and bottom portion 160 may be made from a substantially rigid material, such as thermoformed plastic, to provide support when storing and/ or removing items from the first aid kit 20.

As shown in FIGS. 6-10, the preferred embodiment of the first aid kit 20 further comprises at least one handle 260 that is attached to either side of the top 150 or bottom portion 160. In order to allow easy access with both hands, especially when the first aid kit 20 is stored on the lower back of the user, two handles 260 on opposing sides of either portion 150,160 of the first aid kit 20 should be used. When the first aid kit 20 is stored within the carrier, the removably attached ends 130 of the closure straps 120 (depicted in FIG. 5) on either side of the carrier 10 are woven through the aperture 135 (identified in FIGS. 1-2) created between the handle and the side of the top 150 or bottom portion 160 of the first aid kit 20 before being attached at the perimeter of the interior surface of the opposing front or back portion 30, 40 of the carrier 10.

The handle(s) 260 are ideally comprised of a flexible material such as fabric and can be easily accessed by the user, even when the kit 20 is being stored on the back of the user. In a single motion, when the user pulls on either handle 260, the force exerted will disengage the closure strap 120 allowing the first aid kit 20 to be pulled free from the carrier 10.

When the first aid kit 20 is released from the carrier, the top 150 and bottom portions 160 unfold, quickly revealing the interior surface 190 of both portions 150, 160 (as shown in FIG. 7) where medical equipment is stored within the loops 230 and easily accessible.

Figure 10:
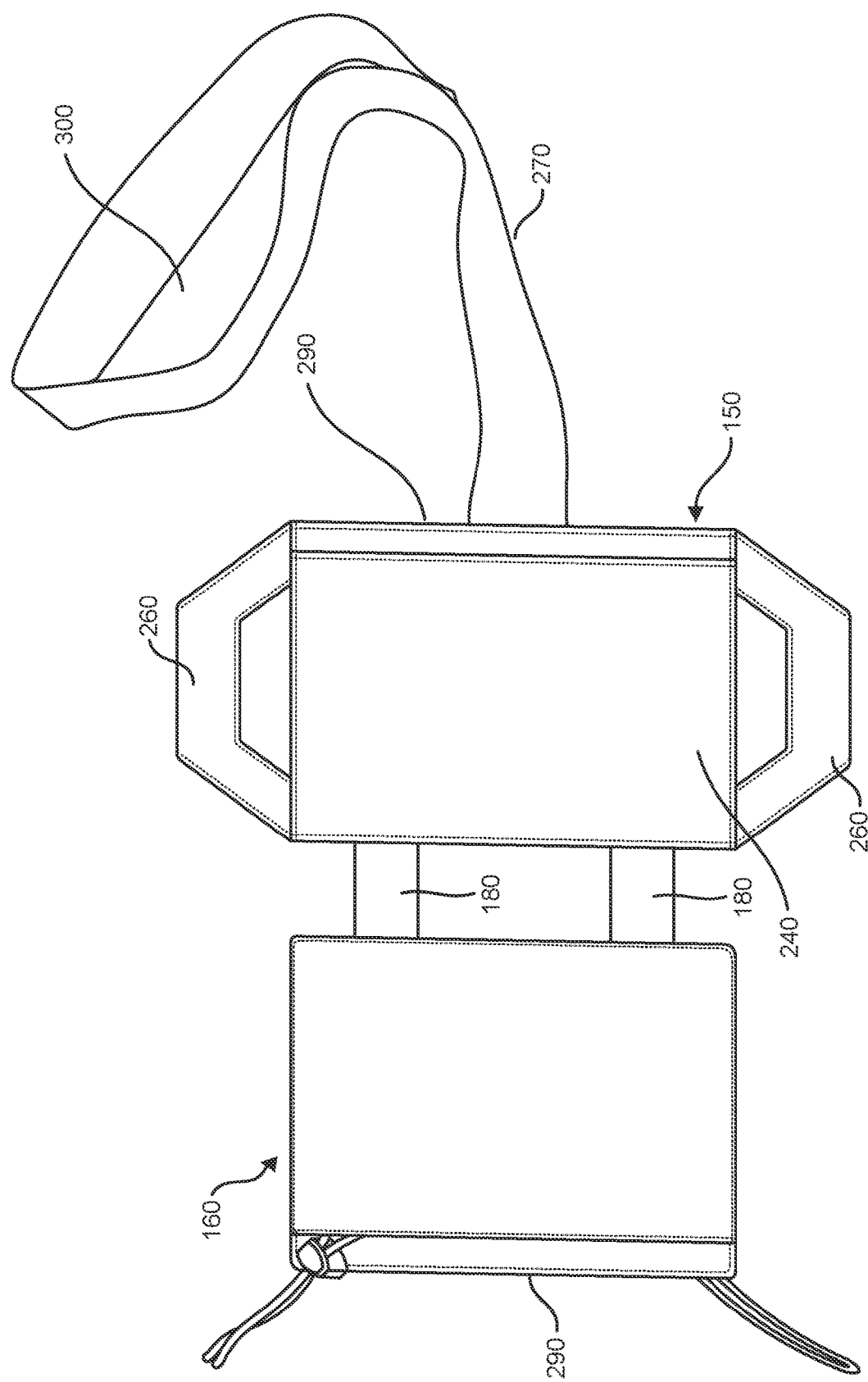
FIG. 10 is a bottom view of the first aid kit in the open, unfolded position.

Turning to FIGS. 7 and 10, the preferred embodiment of the present invention further comprises a carrier strap 270 having two ends wherein one end 280 is attached to the distal end 290 of either the top portion 150 or bottom portion 160 of the first aid kit 20 and the other end is free and further comprises a loop 300, which may be adjustable by means known in the art including by use of a slide adjuster. Although not required, it is preferred that the strap 270 is red to serve as an indicator to the wounded that the device is a medical kit designed to treat the wounded. When it comes to usage, the carrier strap 270 has a dual purpose. First, the carrier strap 270 can be tightly wound around the first aid kit 20 to torque the kit 20 while in the folded, closed position (as shown in FIG. 6). This process not only minimizes the volume the kit 20 will take up within the carrier 10, but also allows for easier re-insertion of the kit 20 into the carrier 10. Second, if the user is unable to take the time to store the kit 20 in the carrier 10, he may simply use the loop 300 to carry the first aid kit 20 by quickly weaving his arm through the loop 300 to carry the kit 20 until such time as the kit 20 can be re-inserted into the carrier 10.

For the purposes of promoting an understanding of the principles of the invention, reference has been made to the preferred embodiments illustrated in the drawings, and specific language has been used to describe these embodiments. However, this specific language intends no limitation of the scope of the invention, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional aspects of the method (and components of the individual operating components of the method) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections might be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A quick-release first aid kit carrying device comprising:
   a. a carrier comprising a front portion, an opposing back portion, and two opposing side connecting members that define a hollow interior compartment;
   b. a first aid kit comprising a top portion, a bottom portion, and a connecting member attached to the proximal ends of said portions with at least one handle attached to the side of either portion that is perpendicular to said proximal ends, wherein the top and bottom portions are foldable along the longitudinal axis of the connecting member, said portions each having an interior and exterior surface further comprising fastening means to attach equipment to either surface;
   c. a carrier strap comprising a length of a material having one end attached to either the distal end of the top portion or bottom portion of the first aid kit and the other end is free and further comprises a loop;
      wherein the carrier strap is sized and dimensioned to wrap around the first aid kit in a folded position and further operable to torque the first aid kit in the folded position so that the first-aid kit can be secured within the interior compartment of the carrier,
      wherein the first aid kit is removably stored within the interior compartment of the carrier,
      wherein the handle allows the first aid kit to be quickly released from the carrier.

2. The device of claim 1 wherein the front portion of the carrier is substantially concave.

3. The device of claim 2 wherein the front portion is substantially rigid.

4. The device of claim 1 further comprising a plurality of mounting apertures on the back portion of the carrier.

5. The device of claim 4 wherein the mounting apertures are adapted to attach to a mounting accessory.

6. The device of claim 5 wherein the mounting accessory is selected from the group comprising paddles, clips, belt loops, MOLLE (modular, lightweight load-carrying equipment) attachment devices, leg mounts, vest carry and harness carry devices.

7. The device of claim 1 further comprising a cover that is attached along either the bottom portion of the first aid kit or the perimeter of the exterior surface of the top portion of the first aid kit.

8. The device of claim 1 wherein the top portion or bottom portion is made from a substantially rigid material, namely thermoformed or injection molded plastic.

9. The device of claim 2 further comprising a cover that is attached along either the bottom portion of the first aid kit or the perimeter of the exterior surface of the top portion of the first aid kit.

10. The device of claim 2 wherein the top portion or bottom portion is made from a substantially rigid material, namely thermoformed or injection molded plastic.

11. The device of claim 1 wherein the loop of the carrier strap is sized and dimensioned to receive an arm of a user for carrying the first aid kit in the unfolded position.

* * * * *